(12) United States Patent
Nardone

(10) Patent No.: US 6,768,000 B1
(45) Date of Patent: Jul. 27, 2004

(54) MULTI-FLUORESCENT HAIRPIN ENERGY TRANSFER OLIGONUCLEOTIDES

(75) Inventor: Glenn Nardone, Oakton, VA (US)

(73) Assignee: Intergen Company, Purchase, NY (US)

( * ) Notice: Subject to any disclaimer, the term of this patent is extended or adjusted under 35 U.S.C. 154(b) by 0 days.

(21) Appl. No.: 09/701,394

(22) PCT Filed: Jun. 11, 1999

(86) PCT No.: PCT/US99/12799

§ 371 (c)(1),
(2), (4) Date: Jan. 17, 2001

(87) PCT Pub. No.: WO99/64432

PCT Pub. Date: Dec. 16, 1999

Related U.S. Application Data

(60) Provisional application No. 60/089,119, filed on Jun. 12, 1998.

(51) Int. Cl.[7] .................. C07H 19/00; C07H 21/04; C12Q 1/68
(52) U.S. Cl. ............. 536/22.1; 536/24.31; 536/24.33; 435/6
(58) Field of Search .................. 536/22.1, 24.31, 536/24.33, 24.32; 435/6

(56) References Cited

U.S. PATENT DOCUMENTS

| | | | |
|---|---|---|---|
| 5,532,129 A | * | 7/1996 | Heller .......................... 435/6 |
| 5,866,336 A | * | 2/1999 | Nazarenko et al. ............ 435/6 |

* cited by examiner

Primary Examiner—Jeffrey Fredman
Assistant Examiner—Suryaprabha Chunduru
(74) Attorney, Agent, or Firm—Foley & Lardner LLP

(57) ABSTRACT

An oligonucleotide, labeled with a molecular energy transfer trio and containing two sequences capable of hairpin formation, is used in the detection of two targets by irradiation with a single wavelength of light. One of the two sequences contains an energy donor and a first energy acceptor, and the other sequence contains a second energy acceptor. The donor is in close proximity to the second acceptor only if the hairpin is formed, while the donor is always in close proximity to first acceptor. A sample is assayed, using this oligonucleotide in conjunction with another oligonucleotide which contains the donor fluorophore and the quencher, arranged as described above, but which lacks the acceptor fluorophore. The present oligonucleotide and the other oligonucleotide are specific to first and second targets, respectively. If a sample contains the first and second targets, then hairpin formation is prevented after each oligonucleotide is incorporated into a target amplification product or hybridized to a target. Subsequent irradiation of the sample with the single wavelength of light which excites the donor fluorophore, but not the acceptor fluorophore, causes two distinctive signals to be generated. The first signal is emitted by the second fluorophore of the present oligonucleotide, while the second signal is emitted by the first fluorophore of the other oligonucleotide. Thus, the first and second targets are detected when one observes the first and second signals, respectively.

2 Claims, No Drawings

SEQUENCE LISTING

<160> NUMBER OF SEQ ID NOS: 5

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
accgatgcgt tgagcatcgg tgaaggtcgg agtcaacgga tt                          42

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 2
agcgatgcgt tcgagcatcg ctgaaggtcg gagtcaacgg att                         43

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 3
agcgatgcgt tcgagcatcg ctgaaggtga ccaagttcat                             40

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 4
ggatctcgct cctggaagat ggt                                               23

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 5
ggtgtacagg gaaggccttt cgggac                                            26

MULTI-FLUORESCENT HAIRPIN ENERGY TRANSFER OLIGONUCLEOTIDES

This application claims the benefit of the U.S. Provisional application No. 60/089,119 filed on Jun. 12, 1998.

BACKGROUND OF THE INVENTION

1. Field of the Invention

The present invention is broadly concerned with an oligonucleotide probe useful for detecting multiple target nucleic acid sequences in a sample. More particularly, the present invention relates to an oligonucleotide probe labeled with a molecular energy transfer (MET) trio including an energy donor and two energy acceptors which makes possible the detection of the multiple targets using only one excitation wavelength of light.

2. Description of the Related Art

The MET phenomenon is a process by which energy is passed between a donor molecule and an acceptor molecule. Fluorescence resonance energy transfer (FRET), which involves at least one fluorophore, is a form of MET. A fluorophore is a compound that absorbs light at one wavelength, and emits light at different wavelength. A spectrofluorimeter is used to simultaneously emit light which excites the fluorophore, and detect light emitted by the fluorophore. In FRET, the fluorophore is a donor molecule which absorbs photons, and subsequently transfers this energy to an acceptor molecule. Donor and acceptor molecules that engage in MET or FRET are termed MET pairs or FRET pairs, respectively. Förster, 1949, Z. Naturforsch A4:321–327; Clegg, 1992, Methods In Enzymology 211:353–388.

When two fluorphores are in close proximity, and the emission spectrum of the first fluorophore overlaps the excitation spectrum of the second fluorophore, excitation of the first fluorophore causes it to emit light that is absorbed by the second fluorophore, which in turn causes the second fluorophore to emit light. As a result, the fluorescence of the first fluorophore is quenched, while the fluorescence of the second flourophore is enhanced. If the energy of the first fluorophore is transferred to a compound that is not a fluorophore, however, the fluorescence of the first fluorophore is quenched without subsequent emission of light by the non-fluorophore.

The FRET phenomenon has been exploited in methods for detecting nucleic acids. One of these methods is disclosed in U.S. Pat. No. 5,866,366, the entire contents of which are herein incorporated by reference. The '366 patent discloses a FRET-labeled hairpin oligonucleotide which is used as a probe in polymerase chain reaction (PCR) methods to detect target nucleic acid sequences. This oligonucleotide contains an energy donor and an energy acceptor constituting a FRET pair. The donor and acceptor are respectively situated on first and second nucleotide sequences of the oligonucleotide. These two nucleotide sequences are complementary to each other, and are therefore able to form a hairpin in the oligonucleotide.

If the first and second nucleotide sequences are annealed to each other, then the donor and acceptor are in close proximity. In this spatial arrangement, the acceptor absorbs the emission from the donor, and thereby quenches the signal from the donor. However, if the nucleotide sequences are not annealed to each other, then the donor and acceptor are separated, the acceptor can no longer absorb the emission from the donor, and the signal from the donor is not quenched.

Thus, if the oligonucleotide is incorporated into an amplification product during PCR, then the hairpin unfolds, resulting in the separation of the donor from the acceptor, and the consequent emission of an observable signal. However, if the oligonucleotide is not incorporated into a PCR amplification product, then the hairpin remains, and the emission from the donor is quenched by the acceptor. Detection of a signal after PCR therefore indicates the presence of the target.

Additionally, the FRET-labeled hairpin oligonucleotide described above may be used as a "molecular beacon" to detect a target nucleic acid sequence without incorporating it into a DNA molecule. The molecular-beacon technology is described in Tyagi et al., 1996, Nature Biotechnology 14:303–308, the entire contents of which are herein incorporated by reference. If the oligonucleotide hybridizes to a target, the hairpin unfolds, and a detectable signal is generated. If the oligonucleotide does not hybridize to the target, the hairpin remains, and the signal is quenched. Detection of a signal after hybridization therefore indicates the presence of the target.

Detection of more than one target nucleic acid molecule in a single sample using the methods disclosed in the '336 patent and Tyagi et al. requires a FRET-labeled hairpin oligonucleotide specific to each target molecule, wherein each donor emits a distinctive signal. Since each donor typically must be excited by a different wavelength of light, it is necessary to irradiate the sample with multiple wavelengths of light. A major drawback to this approach, however, is that it requires a spectrofluorimeter emitting a broad spectrum of light.

SUMMARY OF THE INVENTION

Avoiding the aforementioned drawback, the present invention is directed to a MET-labeled oligonucleotide, as well as to the use of this oligonucleotide to detect multiple target nucleic acid sequences in a single sample. Pursuant to this invention, multiple targets can be detected by irradiating a sample, containing the targets, with a single excitation wavelength of light.

An oligonucleotide according to the present invention contains three nucleotide sequences: a first nucleotide sequence, a second nucleotide sequence at the 5' end of the first nucleotide sequence, and a third nucleotide sequence at the 5' end of the second nucleotide sequence. Additionally, the oligonucleotide contains a MET trio, e.g a FRET trio, that includes an energy donor moiety and first and second energy acceptor moieties, where (i) the energy donor moiety is capable of emitting a quantum of energy and (ii) each of the first and second acceptor moieties is capable of absorbing a substantial amount of the quantum of energy. Preferably, the first acceptor moiety also is capable of emitting a quantum of energy.

The donor moiety is attached to a nucleotide of the first nucleotide sequence, the first acceptor moiety is attached to a nucleotide of the first nucleotide sequence, and the second acceptor moiety is attached to a nucleotide of the third nucleotide sequence, or, alternatively, the donor moiety is attached to a nucleotide of the third nucleotide sequence, the first acceptor moiety is attached to a nucleotide of the third nucleotide sequence, and the second acceptor moiety is attached to a nucleotide of the first nucleotide sequence.

The oligonucleotide is capable of forming a hairpin containing a nucleotide of the first nucleotide sequence and a nucleotide of the third nucleotide sequence. If the donor moiety emits the quantum of energy, then the first acceptor moiety absorbs a substantial amount of the emitted quantum of energy if, preferably only if, the hairpin is not formed, and the second acceptor moiety absorbs a substantial amount of the emitted quantum of energy if, preferably only if, the hairpin is formed.

An oligonucleotide of this invention preferably comprises a fourth nucleotide sequence at the 3' end of the first nucleotide sequence. Ideally, the third nucleotide sequence is not complementary to the fourth nucleotide sequence, and the fourth nucleotide sequence is complementary to a nucleotide sequence flanking a target nucleotide sequence. e.g., a DNA sequence. The oligonucleotide may be included in a kit containing a polymerase. The oligonucleotide preferably comprises a deoxyribonucleotide.

Advantageously, the donor moiety and the first acceptor moiety each are fluorophores, while the second acceptor moiety is a quencher of light emitted by the donor moiety. The preferred donor moiety, first acceptor moiety, and second acceptor moiety are fluorescein, 6-carboxy-X-rhodamine (ROX), and 4-(4'-dimethylamino-phenylazo) benzoic acid (DABSYL), respectively.

Preferably, there is (are) 0 to 50 nucleotide(s) in between the nucleotide to which the donor moiety is attached and the nucleotide to which the first acceptor moiety is attached, and there is (are) 0 to 50 nucleotide(s) in between the nucleotide to which the donor moiety is attached and the nucleotide to which the second acceptor moiety is attached. More preferably, there are 5 to 10 nucleotides in between the nucleotide to which the donor moiety is attached and the nucleotide to which the first acceptor moiety is attached, and there are 5 to 10 nucleotides in between the nucleotide to which the donor moiety is attached and the nucleotide to which the second acceptor moiety is attached.

Advantageously, if the hairpin is formed, then the nucleotide to which the donor moiety is attached is the complement of the nucleotide to which the second acceptor moiety is attached, or there is (are) 0 to 5 nucleotide(s) in between the nucleotide to which the donor moiety is attached and the complement of the nucleotide to which the second acceptor moiety is attached.

A preferred oligonucleotide comprises or consists of the nucleotide sequence of SEQ ID NO:1, wherein fluorescein is attached to the nucleotide at position 1 of SEQ ID NO:1, ROX is attached to the nucleotide at position 21 of SEQ ID NO:1, and DABSYL is attached to the nucleotide at position 5 or 10 of SEQ ID NO:1.

One method of the present invention is a method for determining if a target nucleotide sequence is present in a sample comprising the following steps:

In step (a), a sample is contacted with an oligonucleotide containing a first nucleotide sequence, a second nucleotide sequence at the 5' end of the first nucleotide sequence, and a third nucleotide sequence at the 5' end of the second nucleotide sequence. The oligonucleotide also contains a MET trio including an energy donor moiety, and first and second energy acceptor moieties, wherein the donor moiety is capable of emitting a first quantum of energy, the first and second acceptor moieties are each capable of absorbing a substantial amount of the first quantum of energy, and the first acceptor moiety is capable of emitting a second quantum of energy. The preferred donor moiety, first acceptor moiety, and second acceptor moiety are fluorescein, ROX, and DABSYL, respectively.

The donor moiety is attached to a nucleotide of the first nucleotide sequence, the first acceptor moiety is attached to a nucleotide of the first nucleotide sequence, and the second acceptor moiety is attached to a nucleotide of the third nucleotide sequence, or, alternatively, the first donor moiety is attached to a nucleotide of the third nucleotide sequence, the first acceptor moiety is attached to a nucleotide of the third nucleotide sequence, and the second acceptor moiety is attached to a nucleotide of the first nucleotide sequence.

The oligonucleotide is capable of forming a hairpin containing a nucleotide of the first nucleotide sequence and a nucleotide of the third nucleotide sequence. If the donor moiety emits the first quantum of energy, then the first acceptor moiety absorbs a substantial amount of the emitted first quantum of energy if, preferably only if, the hairpin is not formed, and the second acceptor moiety absorbs a substantial amount of the emitted first quantum of energy if, preferably only if, the hairpin is formed.

In step (b), if the second quantum of energy is detected, then it is determined that the target nucleotide sequence is present in the sample, or if the second quantum of energy is not detected, then it is determined that the target nucleotide sequence is not present in the sample.

A second method of the present invention is a method for determining if a target nucleotide sequence is present in a sample comprising the following steps:

In step (a), a sample is contacted with an oligonucleotide containing a first nucleotide sequence, a second nucleotide sequence at the 5' end of the first nucleotide sequence, and a third nucleotide sequence at the 5' end of the second nucleotide sequence. The oligonucleotide also contains a MET trio including an energy donor moiety, and first and second energy acceptor moieties, wherein the donor moiety is capable of emitting a first quantum of energy, the first and second acceptor moieties are each capable of absorbing a substantial amount of the first quantum of energy, and the first acceptor moiety is capable of emitting a second quantum of energy. The preferred donor moiety, first acceptor moiety, and second acceptor moiety are fluorescein, ROX, and DABSYL, respectively.

The donor moiety is attached to a nucleotide of the first nucleotide sequence, the first acceptor moiety is attached to a nucleotide of the first nucieotide sequence, and the second acceptor moiety is attached to a nucleotide of the third nucleotide sequence, or, alternatively, the first donor moiety is attached to a nucleotide of the third nucleotide sequence, the first acceptor moiety is attached to a nucleotide of the third nucleotide sequence, and the second acceptor moiety is attached to a nucleotide of the first nucleotide sequence.

The oligonucleotide is capable of forming a hairpin containing a nucleotide of the first nucleotide sequence and a nucleotide of the third nucleotide sequence. If the donor moiety emits the first quantum of energy, then the first acceptor moiety absorbs a substantial amount of the emitted first quantum of energy if, preferably only if, the hairpin is not formed, and the second acceptor moiety absorbs a substantial amount of the emitted first quantum of energy if, preferably only if, the hairpin is formed.

In step (b), the oligonucleotide is incorporated, preferably using a polymerase, into a double-stranded nucleic acid if the target nucleotide sequence is present in the sanmple, thereby preventing the hairpin from forming.

In step (c), which is optional, an amplification reaction is conducted, resulting in the incorporation of the oligonuceotide into an amplification product if the target nucleotide sequence is present in the sample.

In step (d), if the second quantum of energy is detected, then it is determined that the target nucleotide sequence is present in the sample, or if the second quantum of energy is not detected, then it is determined that the target nucleotide sequence is not present in the sample.

A third method of the present invention is a method for detecting a target nucleotide sequence comprising the following steps:

In step (a), a first oligonucleotide is annealed to a nucleotide sequence flanking a target nucleotide sequence, wherein the first oligonucleotide contains a first nucleotide sequence, a second nucleotide sequence at the 5' end of the first nucleotide sequence, and a third nucleotide sequence at the 5' end of the second nucleotide sequence. The first oligonucleotide also contains a MET trio including an energy donor moiety, and first and second energy acceptor moieties, wherein the donor moiety is capable of emitting a first quantum of energy, and the first and second acceptor moieties are each capable of absorbing a substantial amount of the first quantum of energy. The preferred donor moiety, first acceptor moiety, and second acceptor moiety are fluorescein, ROX, and DABSYL, respectively.

The donor moiety is attached to a nucleotide of the first nucleotide sequence, the first acceptor moiety is attached to a nucleotide of the first nucleotide sequence, and the second acceptor moiety is attached to a nucleotide of the third nucleotide sequence, or, alternatively, the donor moiety is attached to a nucleotide of the third nucleotide sequence, the first acceptor moiety is attached to a nucleotide of the third nucleotide sequence, and the second acceptor moiety is attached to a nucleotide of the first nucleotide sequence.

The first oligonucleotide is capable of forming a hairpin containing a nucleotide of the first nucleotide sequence and a nucleotide of the third nucleotide sequence. If the donor moiety emits the first quantum of energy, then the first acceptor moiety absorbs a substantial amount of the emitted first quantum of energy if, preferably only if, the hairpin is not formed, and the second acceptor moiety absorbs a substantial amount of the emitted first quantum of energy if, preferably only if, the hairpin is formed.

The oligonucleotide advantageously comprises a fourth nucleotide sequence at the 3' end of the first nucleotide sequence. Ideally, the third nucleotide sequence is not complementary to the fourth nucleotide sequence, and the fourth nucleotide sequence is complementary to a nucleotide sequence flanking a target nucleotide sequence.

In step (b), the 3' end of the first oligonucleotide is extended using the target nucleotide sequence as a template to form an extended first strand, wherein the target nucleotide sequence is annealed to the extended first strand.

In step (c), the target nucleotide sequence is separated from the extended first strand.

In step (d), the second oligonucleotide is annealed to the extended first strand.

In step (e), the 3' end of the second oligonucleotide is extended using the extended first strand as a template to form an extended second strand, wherein the extended first strand is annealed to the extended second strand.

In step (f), which is optional, the extended first and second strands are amplified.

In step (g), a second quantum of energy emitted by the first acceptor moiety is detected to detect the target nucleotide sequence.

A variety of amplification methods can be used in step (f) to amplify the extended first and second strands (e.g., PCR amplification, strand displacement amplification, and cascade rolling circle amplification). The preferable method of amplification is PCR amplification comprising the following four steps:

In step (1), the extended first strand is separated from the extended second strand.

In step (2), the first oligonucleotide is annealed to the extended second strand, and the second oligonucleotide is annealed to the extended first strand.

In step (3), the 3' end of the first oligonucleotide is extended using the extended second strand as a template to form another extended first strand, wherein the extended second strand is annealed to the other extended first strand. Additionally, the 3' end of the second oligonucleotide is extended using the extended first strand as a template to form another extended second strand, wherein the extended first strand is annealed to the other extended second strand.

In step (4), steps (1), (2), and (3) are repeated for a finite number of times, wherein, in step (1), the extended first and second strands respectively are the extended first strand and the other extended second strand of step (3), or respectively are the other extended first strand and the extended second strand of step (3).

A fourth method of the present invention is a method for detecting a target nucleotide sequence comprising the following steps:

In step (a), a first oligonucleotide is annealed to a nucleotide sequence flanking a target nucleotide sequence, wherein the first oligonucleotide contains a first nucleotide sequence complementary to the nucleotide sequence flanking the target nucleotide sequence, and a second nucleotide sequence at the 5' end of the first nucleotide sequence.

In step (b), the 3' end of the first oligonucleotide is extended using the target nucleotide sequence as a template to form an extended first strand, wherein the target nucleotide sequence is annealed to the extended first strand.

In step (c), the target nucleotide sequence is separated from the extended first strand.

In step (d), a second oligonucleotide is annealed to the extended first strand.

In step (e), the 3' end of the second oligonucleotide is extended using the extended first strand as a template to form an extended second strand, wherein the extended first strand is annealed to the extended second strand.

In step (f), the extended first strand is separated from the extended second strand.

In step (g), a third oligonucleotide is annealed to the extended second strand, wherein the third oligonucleotide contains a first nucleotide sequence, a second nucleotide sequence at the 5' end of the first nucleotide sequence, a third nucleotide sequence at the 5' end of the second nucleotide sequence, and a fourth nucleotide sequence at the 3' end of the first nucleotide sequence. The third oligonucleotide also contains a MET trio comprising an energy donor moiety, and first and second energy acceptor moieties. The donor moiety is capable of emitting a quantum of energy, and the first and second acceptor moieties are each capable of absorbing a substantial amount of the quantum of energy. The preferred donor moiety, first acceptor moiety, and second acceptor moiety are fluorescein, ROX, and DABSYL, respectively.

The donor moiety is attached to a nucleotide of the first nucleotide sequence, the first acceptor moiety is attached to a nucleotide of the first nucleotide sequence, and the second acceptor moiety is attached to a nucleotide of the third nucleotide sequence, or, alternatively, the donor moiety is attached to a nucleotide of the third nucleotide sequence, the first acceptor moiety is attached to a nucleotide of the third nucleotide sequence, and the second acceptor moiety is attached to a nucleotide of the first nucleotide sequence.

The third oligonucleotide is capable of forming a hairpin containing a nucleotide of the first nucleotide sequence and a nucleotide of the third nucleotide sequence, and if the donor moiety emits the quantum of energy, then the first acceptor moiety absorbs a substantial amount of the emitted quantum of energy if, preferably only if, the hairpin is not formed, and the second acceptor moiety absorbs a substantial amount of the emitted quantum of energy if, preferably only if, the hairpin is formed.

The fourth nucleotide sequence is complementary to the complement of the second sequence of the first oligonucleotide. Ideally, the third nucleotide sequence is not complementary to the fourth nucleotide sequence, and the fourth nucleotide sequence is complementary to a nucleotide sequence flanking a target nucleotide sequence.

In step (h), the 3' end of the third oligonucleotide is extended using the extended second strand as a template to form a doubly extended first strand, wherein the doubly extended first strand is annealed to the extended second strand.

In step (i), the doubly extended first strand is separated from the extended labeled second strand.

In step (j), the second oligonucleotide is annealed to the doubly extended first strand.

In step (k), the 3' end of the second oligonucleotide is extended using the doubly extended first strand as a template to form a doubly extended second strand, wherein the doubly extended first strand is annealed to the doubly extended second strand.

In step (1), which is optional, the doubly extended first and second strands are amplified.

In step (m), a second quantum of energy emitted by the first acceptor moiety is detected to detect the target nucleotide sequence.

A variety of amplification methods can be used in step (1) to amplify the extended first and second strands (e.g., PCR amplification, strand displacement amplification, and cascade rolling circle amplification). The preferable method of amplification is PCR amplification comprising the following four steps:

In step (1), the doubly extended first strand is separated from the doubly extended second strand.

In step (2), the second oligonucleotide is annealed to the doubly extended first strand, and the third oligonucleotide is annealed to the doubly extended second strand.

In step (3), the 3' end of the second oligonucleotide is extended using the doubly extended first strand as a template to form another doubly extended second strand, wherein the doubly extended first strand is annealed to the other doubly extended second strand. Additionally, the 3' end of the third oligonucleotide is extended using the doubly extended second strand as a template to form another doubly extended first strand, wherein the doubly extended second strand is annealed to the other doubly extended first strand.

In step (4), steps (1), (2), and (3) are repeated for a finite number of times, wherein, in step (1), the doubly extended first and second strands respectively are the doubly extended first strand and the other doubly extended second strand of step (3), or respectively are the other doubly extended first strand and the doubly extended second strand of step (3).

A fifth method of the present invention is a method for determining if a first or second target nucleotide sequence is present in a sample comprising the following steps:

In step (a), the sample is contacted with first and second oligonucleotides. The first oligonucleotide contains a first nucleotide sequence, a second nucleotide sequence at the 5' end of the first nucleotide sequence, and a third nucleotide sequence at the 5' end of the second nucleotide sequence. The first oligonucleotide also contains a MET trio including a first energy donor moiety, and first and second energy acceptor moieties, wherein the first donor moiety is capable of emitting a first quantum of energy, and the first and second acceptor moieties are each capable of absorbing a substantial amount of the first quantum of energy.

The first donor moiety is attached to a nucleotide of the first nucleotide sequence, the first acceptor moiety is attached to a nucleotide of the first nucleotide sequence, and the second acceptor moiety is attached to a nucleotide of the third nucleotide sequence, or, alternatively, the first donor moiety is attached to a nucleotide of the third nucleotide sequence, the first acceptor moiety is attached to a nucleotide of the third nucleotide sequence, and the second acceptor moiety is attached to a nucleotide of the first nucleotide sequence.

The first oligonucleotide is capable of forming a first hairpin containing a nucleotide of the first nucleotide sequence and a nucleotide of the third nucleotide sequence. If the first donor moiety emits the first quantum of energy, then the first acceptor moiety absorbs a substantial amount of the emitted first quantum of energy if, preferably only if, the first hairpin is not formed, and the second acceptor moiety absorbs a substantial amount of the emitted first quantum of energy if, preferably only if, the first hairpin is formed.

The second oligonucleotide contains a fourth nucleotide sequence, a fifth nucleotide sequence at the 5' end of the fourth nucleotide sequence, a sixth nucleotide sequence at the 5' end of the fifth nucleotide sequence. The second oligonucleotide also contains a MET pair including a second energy donor moiety and a third energy acceptor moiety, wherein the second donor moiety is capable of emitting a second quantum of energy, and the third acceptor moiety is capable of absorbing a substantial amount of the second quantum of energy.

The second donor moiety is attached to a nucleotide of the fourth nucleotide sequence and the third acceptor moiety is attached to a nucleotide of the sixth nucleotide sequence, or, alternatively, the second donor moiety is attached to a nucleotide of the sixth nucleotide sequence and the third acceptor moiety is attached to a nucleotide of the fourth nucleotide sequence.

The second oligonucleotide is capable of forming a second hairpin containing a nucleotide of the fourth nucleotide sequence and a nucleotide of the sixth nucleotide sequence. If the second donor moiety emits the second quantum of energy, then the third acceptor moiety absorbs a substantial amount of the emitted second quantum of energy if, preferably only if, the second hairpin is formed.

The preferred first and second donor moieties each are fluorescein, the preferred first acceptor moiety is ROX, and the preferred second and third acceptor moieties each are DABSYL. Ideally, the first oligonucleotide comprises a seventh nucleotide sequence at the 3' end of the first nucleotide sequence, the third nucleotide sequence is not complementary to the seventh nucleotide sequence, the seventh nucleotide sequence is complementary to a nucleotide sequence flanking the first target nucleotide sequence, the second oligonucleotide further comprises an eighth nucleotide sequence at the 3' end of the fourth nucleotide sequence, the sixth nucleotide sequence is not complementary to the eighth nucleotide sequence, and the eighth nucleotide sequence is complementary to a nucleotide sequence flanking the second target nucleotide sequence.

In step (b) the first oligonucleotide is incorporated, preferably using a polymerase, into a first double-stranded nucleic acid if the first target nucleotide sequence is present in the sample, thereby preventing the first hairpin from forming. Additionally, the second oligonucleotide is incorporated, preferably using a polymerase, into a second double-stranded nucleic acid if the second target nucleotide sequence is present in the sample, thereby preventing the second hairpin from forming.

In step (c), which is optional, a first amplification reaction is conducted, thereby incorporating the first oligonucleotide into a first amplification product if the first target nucleotide sequence is present in the sample. Additionally, a second amplification reaction is conducted, thereby incorporating the second oligonucleotide into a second amplification product if the second target nucleotide sequence is present in the sample.

In step (d), it is determined that the first target nucleotide sequence is present in the sample if a third quantum of energy emitted by the first acceptor moiety is detected, or it is determined that the first target nucleotide sequence is not present in the sample if the third quantum of energy is not detected. Additionally, it is determined that the second target nucleotide sequence is present in the sample if a fourth quantum of energy emitted by the third acceptor moiety is detected, or it is determined that the second target nucleotide sequence is not present in the sample if the fourth quantum of energy is not detected.

Other objects, features, and advantages of the present invention will become apparent from the following detailed description. It should be understood, however, that the description and the specific examples, while indicating preferred embodiments of the invention, are given by way of illustration only, because various changes and modifications within the spirit and scope of the invention will become apparent to those skilled in the art from this detailed description.

DETAILED DESCRIPTION OF THE PREFERRED EMBODIMENT

As explained above, the oligonucleotide of the present invention contains two nucleotide sequences that are capable of hybridizing to each other to form a hairpin. One nucleotide sequence contains an energy donor and first energy acceptor, while the other nucleotide sequence contains a second energy acceptor that is able to quench the signal generated by the donor. Thus, the present oligonucleotide contains a MET trio. In a preferred embodiment, the donor and first acceptor are fluorophores, the emission spectrum of the donor fluorophore overlaps the excitation spectrum of the acceptor fluorophore (i.e., the first acceptor), and the second acceptor is a quencher of the signal emitted by the donor fluorophore.

In accordance with the present invention, the donor fluorophore and the quencher are positioned on the oligonucleotide so that, if the hairpin is formed, then the donor fluorophore is in close proximity to the quencher, and energy emitted by the donor fluorophore is absorbed by the quencher, resulting in quenching of the signal from the donor fluorophore. If the hairpin is not formed, however, and the quencher consequently does not absorb the energy emitted by the donor, then the emitted energy is absorbed by the acceptor fluorophore, and is subsequently emitted by the acceptor fluorophore as a detectable signal.

Pursuant to the present invention, detection of a target nucleic acid sequence in a sample occurs in one of at least two ways. First, the oligonucleotide may be incorporated into an amplification product which contains the target sequence. Second, the oligonucleotide may be hybridized to the target sequence. In a preferred embodiment, irradiation of the sample, using a spectrofluorimeter after such incorporation or hybridization, causes the acceptor fluorophore to emit a signal which is detected by the spectrofluorimeter. Thus, signal detection indicates that the target is present, while the absence of a signal indicates that the target is not present.

A sample is assayed for the presence of two targets by using the oligonucleotide described above in conjunction with another oligonucleotide. The other oligonucleotide also contains two nucleotide sequences capable of forming a hairpin, along with a donor fluorophore and a quencher positioned, with respect to the hairpin, as in the present oligonucleotide. The donors of the present oligonucleotide and the other oligonucleotide are excited by the same or approximately the same wavelength of light. However, the other oligonucleotide does not contain the acceptor fluorophore, and therefore contains a MET pair rather than a MET trio. The present oligonucleotide and other oligonucleotide are specific to the first and second targets, respectively.

If the sample contains both the first and second targets, then a hairpin is prevented from forming in both the present oligonucleotide and the other oligonucleotide after the amplification or hybridization reactions are conducted. Subsequent irradiation of the sample with a single wavelength of light that excites the donor fluorophore of the present oligonucleotide and the other oligonucleotide, but not the acceptor fluorophore of the present oligonucleotide, causes two distinctive signals to be generated. The first signal is emitted by the acceptor moiety of the present oligonucleotide, while the second signal is emitted by the donor fluorophore of the other oligonucleotide. Thus, the first target is detected by observing the first signal, while the second target is detected by observing the second signal. Two targets therefore can be detected by irradiating the sample with only one wavelength of light.

The invention is further described by reference to the examples below, with are set forth by illustration only. Nothing therein should be taken as a limitation upon the overall scope of the invention.

EXAMPLE 1

Spectroscopic analysis of model FRET-labeled hairpin oligonucleotides each containing a donor fluorophore, an acceptor fluorophore, and a quencher A total of seven oligonucleotides were synthesized. All of these oligonucleotides have the following nucleotide sequence: 5'-ACCGATGCGTTGAGCATCGGTGAAGGT CGGAGTCAACGGATT-3' (SEQ ID NO:1). All of the oligonucleotides contain a fluorescein moiety (i.e., the first fluorophore) attached to the nucleotide at position 1 and a DABSYL moiety attached to the nucleotide at position 21. Oligonucleotides 1 through 4 each contain a second fluorophore attached to the nucleotide at position 5, while oligonucleotides 5 through 7 each contain a second fluorophore attached to the nucleotide at position 10. The second fluorophore in oligonucleotides 1 and 5 is N,N,N',N'-tetramethyl-6-carboxyrhodamine (TAMRA), in oligonucleotides 3 and 6 is ROX, in oligonucleotides 4 and 7 is Texas Red, and in oligonucleotide 2 is Bodipy 564/570.

The fluorescein and DABSYL moieties were incorporated into each oligonucleotide during their synthesis using a dA-fluorescein phosphoramidite and a dU-DABSYL phosphoroamidite, respectively. Additionally, a hexylamine moiety was attached to the carbon atom at the 5 position of the base moiety of the nucleotides at position 5 of oligonucleotides 1 through 4, and at position 10 of oligonucleotides 5 through 7. This hexylamine moiety was incorporated into each oligonucleotide during their synthesis using a dU-hexylamine phosphoramidite.

After the oligonucleotides were synthesized as describe above, each oligonucleotide was deprotected, desalted, and purified by reverse-phase high-performance liquid chromatography using C18 silica and triethylamine acetate-acetonitrile gradients. The appropriate fractions were subsequently pooled, precipitated using acetone, dried under vacuum, dissolved, and desalted.

The hexylamine residue of each oligonucleotide was then labeled with the appropriate fluorophore containing an N-succinimidyl ester or an isothiocyanate moiety in a solution of sodium bicarbonate buffer, pH 9, 20% dimethyl sulfoxide at room temperature for approximately 20 hours. Each oligonucleotide was subsequently precipitated using acetone, dried under vacuum, dissolved, and desalted.

For spectroscopic analysis of each of the oligonucleotides, four to five picomoles of oligonucleotide were dissolved in a volume of 0.6 ml. Each oligonucleotide solution was analyzed using a Shimadzu RFU 5000 analytical spectrofluorimeter. To induce the closed confirmation, in which the oligonucleotide contains a hairpin, the oligonucleotide was dissolved in annealing buffer containing 10 mM Tris-HCl, pH 8, 3 mM $MgCl_2$, and 50 mM NaCl. The open confirmation, in which the hairpin is absent, was induced by adding a molar excess of a complementary, unlabeled oligonucleotide to each oligonucleotide in annealing buffer, heating the solution at 90° C. for three minutes, and cooling the solution to room temperature.

The fluorescein moiety of each oligonucleotide in the open and closed conformations was excited by irradiation. Table 1 below demonstrates that such irradiation results in a substantial light emission from the second fluorophore of each oligonucleotide in the open conformation. In the closed conformation, however, each oligonucleotide shows little second-fluorophore emission at fluorescein excitation wavelengths.

TABLE 1

| oligo-nucleotide | second fluorophore | excitation wavelength $(nm)^1$/ emission wavelength $(nm)^2$ | fluorescence per picomole in closed conformation (relative fluoresence units) | fluorescence per picomole in open conformation (relative fluoresence units) |
| --- | --- | --- | --- | --- |
| 1 | TAMRA | 495/588 | 6 | 28 |
| 2 | Bodipy 564/570 | 495/598 | 7 | 48 |
| 3 | ROX | 495/605 | 3 | 34 |
| 4 | Texas Red | 495/620 | 5 | 26 |
| 5 | TAMRA | 495/588 | 7 | 30 |
| 6 | ROX | 495/605 | 4 | 18 |
| 7 | Texas Red | 495/620 | 4 | 30 |

[1] Wavelength of light exciting fluorescein.
[2] Wavelength of light emitted from the second fluorophore; the wavelength of each second-fluorophore emission is substantially different from the peak wavelength of fluorescein emission (516 nm).

EXAMPLE 2

Detection of two target nucleic acid sequences in PCR amplification using a hairpin oligonucleotide containing a FRET trio and a hairpin oligonucleotide containing a FRET pair.

A sample is assayed for the presence of mRNA encoded by a prostate-specific antigen (PSA) gene. As a control to insure that a PCR reaction can be conducted in the sample, a quantity of cDNA specific to the glyceraldehyde-3-phosphate dehydrogenase (gapDH) gene is added to the sample.

The hairpin oligonucleotides are used as forward primers during PCR. The nucleotide sequence of the forward primer specific to the gapDH cDNA is 5'-AGCGATGCGTTCG AGCATCGCTGAAGGTCGGAGTCAACGGATT-3' (SEQ ID NO:2), wherein the nucleotides at positions 1 and 22 are labeled with fluorescein and DABSYL, respectively, and the nucleotide at position 5 or 10 is labeled with TAMRA. The nucleotide sequence of the hairpin primer specific to the PSA mRNA is 5'-AGCGATGCGTTCGAGCATCGCTGAA GGTGACCAAGTTCAT-3' (SEQ ID NO:3), wherein the nucleotides at positions 1 and 22 are labeled with fluorescein and DABSYL, respectively. The nucleotide sequences of the reverse primers specific to the gapDH cDNA and the PSA mRNA are 5'-GGATCTCGCTCCTGGAAGATGGT-3' (SEQ ID NO:4), and 5'-GGTGTACAGGGAAGGC CTTTCGGAC-3' (SEQ ID NO:5), respectively.

Each PCR reaction sample contains, in a 0.2 ml PCR reaction tube, 10 mM Tris-HCl, pH 8.3, 50 mM KCl, 1.5 mM $MgCl_2$, 250 µm dNTPs, 0.25 µm of each forward primer, 0.25 µm of each reverse primer, gapDH cDNA, and 2 units of Taq polymerase in 50 µl. A control sample additionally contains PSA mRNA, which, for example, is produced by LNCaP tissue-culture cells available from the American Type Culture Collection, Manassas, Va.

Each reaction tube is placed in a thermocycler such as an ABI 7700 real-time instrument, or a Perkin Elmer 9600 or 9700. The cycle program is as follows: [94° C., 4 min.]–[94° C, 15 sec.; 55° C., 30 sec.; 72° C., 1 min]for 35 cycles—[72° C., 5min]–[4° C., hold]. The progress of gapDH cDNA amplification is followed directly by observing the emission of light having a wavelength of 580 nm (i.e., the emission from TAMRA), while the progress of PSA mRNA amplification is followed directly by observing the emission of light having a wavelength of 530 nm (the emission from fluorescein). End-point analysis is effected by means of a fluorescent plate reader, such as a Wallac Victor equipped with filters that allow detection of 530-nm and 580-nm light.

This application claims priority from U.S. provisional application serial No. 60/089,119, entitled "MULTI-FLUORESCENT HAIRPIN ENERGY TRANSFER OLIGONUCLEOTIDES," which was filed on Jun. 12, 1998. The entire contents of this application are incorporated herein by reference.

I claim:

1. An oligonucleotide comprising the nucleotide sequence of SEQ ID NO:1, wherein fluorescein is attached to the nucleotide at position 1 of SEQ ID NO:1, ROX is attached to the nucleotide at position 21 of SEQ ID NO:1, and DABSYL is attached to the nucleotide at position 5 or 10 of SEQ ID NO:1.

2. The oligonucleotide of claim 1 consisting of the nucleotide sequence of SEQ ID NO:1.

* * * * *